(12) United States Patent
Hamilton

(10) Patent No.: US 7,789,911 B2
(45) Date of Patent: Sep. 7, 2010

(54) PROSTHESIS AND METHOD OF MANUFACTURING A PROSTHESIS

(75) Inventor: Jonathan Hamilton, Honeydew (ZA)

(73) Assignee: Smart Implant PLC, London (GB)

( * ) Notice: Subject to any disclaimer, the term of this patent is extended or adjusted under 35 U.S.C. 154(b) by 0 days.

(21) Appl. No.: 11/883,217

(22) PCT Filed: Jan. 27, 2006

(86) PCT No.: PCT/IB2006/000142

§ 371 (c)(1),
(2), (4) Date: Sep. 5, 2008

(87) PCT Pub. No.: WO2006/079908

PCT Pub. Date: Aug. 3, 2006

(65) Prior Publication Data

US 2009/0043385 A1    Feb. 12, 2009

(30) Foreign Application Priority Data

| Jan. 29, 2005 | (ZA) | ................... 2004/8765 |
| Jan. 29, 2005 | (ZA) | ................. 2004/10188 |
| Apr. 20, 2005 | (ZA) | ................... 2005/3184 |
| May 27, 2005 | (ZA) | ................... 2005/4333 |
| Aug. 22, 2005 | (ZA) | ................... 2005/6704 |
| Sep. 14, 2005 | (ZA) | ................... 2005/7390 |
| Oct. 21, 2005 | (ZA) | ................... 2005/8552 |
| Nov. 17, 2005 | (ZA) | ................... 2005/9314 |

(51) Int. Cl.
*A61F 2/12* (2006.01)

(52) U.S. Cl. ......................................................... 623/8
(58) Field of Classification Search .................. 623/7–8
See application file for complete search history.

(56) References Cited

U.S. PATENT DOCUMENTS

| 3,934,274 | A | * | 1/1976 | Hartley, Jr. | ..................... 623/8 |
| 4,264,990 | A | * | 5/1981 | Hamas | .......................... 623/8 |
| 4,636,213 | A | | 1/1987 | Pakiam | |
| 4,863,470 | A | * | 9/1989 | Carter | ........................... 623/8 |
| 4,969,899 | A | * | 11/1990 | Cox, Jr. | ......................... 623/8 |
| 5,300,120 | A | * | 4/1994 | Knapp et al. | ............ 623/11.11 |
| 6,432,138 | B1 | * | 8/2002 | Offray et al. | ................... 623/8 |
| 2004/0162613 | A1 | * | 8/2004 | Roballey | ........................ 623/8 |

FOREIGN PATENT DOCUMENTS

EP        0 619 101 A1    10/1994

OTHER PUBLICATIONS

International Preliminary Report on Patentability in corresponding PCT/IB06/000142 dated Jul. 31, 2007.
Written Opinion in corresponding PCT/IB06/000142 dated Jul. 31, 2007.

* cited by examiner

*Primary Examiner*—Suzette J Gherbi
(74) *Attorney, Agent, or Firm*—Marshall, Gerstein & Borun LLP

(57) ABSTRACT

A human prosthesis, in particularly a human mammary prosthesis, is disclosed which includes a resilient shell at least partly filled with a fluid filler material and having at least one resilient layer and at least one layer being substantially non-permeable with respect to at least the filler material of the shell, and with the filler material being fluid based.

15 Claims, 1 Drawing Sheet

PROSTHESIS AND METHOD OF MANUFACTURING A PROSTHESIS

FIELD OF THE INVENTION

This invention relates to a prosthesis in particular but not limited to a human mammary prosthesis.

BACKGROUND TO THE INVENTION

Mammary prostheses are used to enhance the appearance of human breasts, normally female breasts. The prostheses are used to add volume to a breast which may be required after removal of a tumour, or to enhance the aesthetic appeal of a breast.

A mammary prosthesis typically comprises a resilient plastics material bladder which is filled with a liquid. The bladder is normally manufactured from a silicone rubber filled with a gel, typically a silicone gel.

A problem with silicone gel is rupturing of the bladder which releases the gel in the patient's body. If a bladder ruptures in vitro the released gel cannot be recovered, or at least not all of it.

A serious complication of silicone gel filled bladder prostheses is capsular contraction, which is a condition in which tissue surrounding the prosthesis after it has been implanted into a patient hardens. This hardening of the tissue takes place in response to silicone gel which routinely leaks through the bladder. The leaking is an accepted side effect of these prostheses and capsulation is, in part, relied upon to contain silicone which leaks from the bladder.

One likely driving force for the bleed of the filler material, and specifically silicone gel, is Brownian motion, which is a result of thermal molecular motion of particles in a liquid environment. According to this phenomenon, there is random movement of the silicone gel particles inside the shell of the prosthesis. Since the atomic structure of solid silicone, from which the shell of the prosthesis is manufactured, is larger than the size of silicone gel molecules, some of the gel molecules will pass through the shell because of the Brownian motion. In essence, the shell is like a mesh through which the gel particles can be squeezed.

Another phenomenon which also likely acts as a driving force is osmotic pressure. According to Merriam-Webster's Collegiate Dictionary, osmosis is the "movement of a solvent through a semi-permeable membrane (as of a living cell) into a solution of higher solute concentration that tends to equalize the concentrations of solute on the two sides of the membrane." In the case of a silicone gel filled mammary prosthesis, there is a higher concentration of gel inside the shell of the prosthesis than outside the shell. Body fluid, of which there is plenty in supply, will tend to move into the prosthesis because of osmotic pressure in an attempt to equalize the concentrations of silicone gel on opposite sides of the shell. This increases the fluid pressure inside the prosthesis which contributes as a driving force to push fluids out of the prosthesis, including silicone gel. At the same time the silicone gel, which is at a higher concentration inside the shell than in the human body and is at least to some degree a solute, experiences osmotic pressure to move from a higher concentration to a lower concentration through the shell, i.e. from the prosthesis into the body.

There have been attempts to limit the spread of the silicone by formulating it as a 'sticky' gel. The intention with this is to keep the silicone gel together and to ease surgical removal. However, this does not solve the problem since the sticky gel adheres to anything it touches including the patient's organs and the surgeon's gloves. Removing the sticky gel is not an easy matter and 100% removal of all leaked gel is generally not possible.

In some countries, the use of bladders filled with silicone gel has been banned due to the health risks associated with it. To overcome this problem prostheses have been developed which comprise a bladder filled with liquid other than silicone gel, for example saline solution. This solves the problem of the leaking which causes capsular contraction. If such a prosthesis ruptures the patient doesn't need surgery to remove the liquid, since saline is harmless to the human body.

A problem associated with saline filled prostheses is that these prostheses are generally inserted empty into a patient and filled in vitro by means of a filler tube and non return valve. These systems are often problematic and leakage of saline through the filler tube arrangement often occurs.

Another problem with saline filled prostheses is that the viscosity of saline is different from silicone gel, which causes these prostheses to have an unnatural feel once implanted.

Another problem with conventional prostheses is that details of implanted prostheses are not readily ascertainable from outside the body. In some instances it is necessary to determine details, such as size and type of implant or the date on which the prostheses was implanted on short notice and preferably without surgical procedure. Such instances may include a medical emergency such as may arise following an accident. It may also occur during routine procedures.

It often happens that people are unable to convey details of a prosthesis to medical personnel which may leave the medical personnel with no option but to determine details of the implanted prosthesis by means of expensive scanning equipment, for example MRI scanning, or surgery. Neither of these is desirable, the first due to the cost involved and second due to the invasive and drastic nature and the cost thereof.

A specific problem exists with female patients whom had received breast augmentation surgery and experience complications. In many instances, these patients are not able to recall the make of prosthesis they have received and in even more cases, not the size of prosthesis received. If an existing prosthesis needs to be replaced the surgeon needs to have all possible sizes available during surgery to fit the correct size prosthesis.

A further aspect of breast prostheses that is problematic relates to the manufacturing of the prostheses. In most cases a bladder is formed which include an opening at the operatively posterior side of the bladder. This opening is needed in the forming of the bladder to enable removal from the mould on which the bladder is formed. The opening is sealed by means of a disc which is placed inside the opening and adhered to the bladder by means of pressure. A problem with this type of seal is that it is not a seal that is formed by means of a bond between the two surfaces forming part of the seal, but rather an adhesion type seal of the disc against the bladder which, after the bladder has been filled, relies on pressure from the gel inside the bladder to maintain the seal. It is possible to disengage such a seal by exerting on the disc from the outside.

The above mentioned problems have been exemplified by way of a mammary prosthesis, but similar problems exist with other types of prostheses. Examples of these include prostheses which are used to enhance the appearance of buttocks, cheeks, and biceps. The concerns about the safety of silicone gel filled prostheses are equally applicable to these procedures, as are problems which exist with saline filled prostheses.

OBJECT OF THE INVENTION

It is an object of the invention to provide a prosthesis which at least partly overcomes the abovementioned problems.

SUMMARY OF THE INVENTION

In accordance with this invention there is provided a human prosthesis comprising a resilient shell at least partly filled with a fluid filler material, for the shell to comprise at least one resilient layer and at least one layer being substantially non-permeable with respect to at least the filler material of the shell, and for the filler material to comprise in particular a silicone gel or a saline based fluid.

There is further provided for the resilient layer to comprise a sealed operatively outer container, for the non-permeable layer to comprise a sealed operatively inner container which contains the filler material and for the inner container to be contained by the outer container, and preferably for the prosthesis to include a lubricant between the inner container and outer container.

There is still further provided for the non-permeable layer to be non-permeable also with respect to body fluids.

There is still further provided for the surface area of the inner container to be greater than the surface area of the outer container, and preferably at least twice as large, alternatively for the surface area of the inner container to be at least as great as the maximum surface area to which the outer container may be stretched elastically.

According to a further feature of the invention there is provided for the non-permeable layer to comprise a composite layer, and for the composite layer to comprise a nylon layer located between a polyester and polyethylene layer.

There is still further provided for the lubricant between the inner container and outer container and preferably also for the filler material to include a hydrophilic polymer, preferably a water soluble polymer or hydrogel, and further preferably polyvinyl pyrrolidone (PVP), and for the non-permeable layer to include at least a polyethylene layer.

There is further provided for the hydrophilic polymer to be mixed with a saline solution, and preferably for the lubricant to comprise about 15% hydrophilic polymer and about 85% saline solution.

According to further feature of the invention there is provided for the non-permeable layer to comprise a composite layer which comprises at least a composite polyethylene and aluminium layer, for the filler material to include glycerine, and preferably for the filler material to comprise a combination of water and glycerine.

There is still further provided for the for the aluminium layer to be a vapour deposited layer on the polyethylene layer and for the vapour deposited aluminium layer to have a thickness in the range of about 12 micron to 18 micron.

There is also provided for the non-permeable layer to have a thickness of between about 20 micron and about 70 micron, preferably between about 40 micron and 55 micron, more preferably to have a thickness of about 48 micron.

According to a still further feature of the invention there is provided for the outer container to contain a plurality of inner containers, for each of the plurality of inner containers to contain filler material, and for each inner container to comprise a non-permeable layer including a nylon layer located between a polyester and polyethylene layer, preferably including a hydrophilic polymer; alternatively for each inner container to comprise a non-permeable layer including at least a composite polyethylene and aluminium layer within which the filler material is located, which preferably includes glycerine, preferably a combination of water and glycerine.

According to a yet further feature of the invention the shell has a predetermined shaped corresponding to that of a breast.

There is also provided for the prosthesis to include identification means bearing data relating to at least the size of the prosthesis, and preferably for the identification means to comprise an identification tab on which the data is printed.

According to a further feature of the invention, there provided for the prosthesis to include a remotely activatable data transmission device configured to transmit a predetermined data carrying signal in response to remote activation thereof.

There is further provided for the transmission device to comprise a data transponder, preferably in the form of a Radio Frequency Identification (RFID) tag, and for the RFID to be remotely activatable by means of an energy field, preferably a magnetic field.

There is still further provided for the RFID tag to be incorporated into the shell, alternatively to be incorporated into the filler opening seal of the shell.

BRIEF DESCRIPTION OF THE DRAWINGS

Embodiments of the invention are described by way of example only and with reference to the accompanying drawings in which.

DETAILED DESCRIPTION OF THE INVENTION

Figure 1:
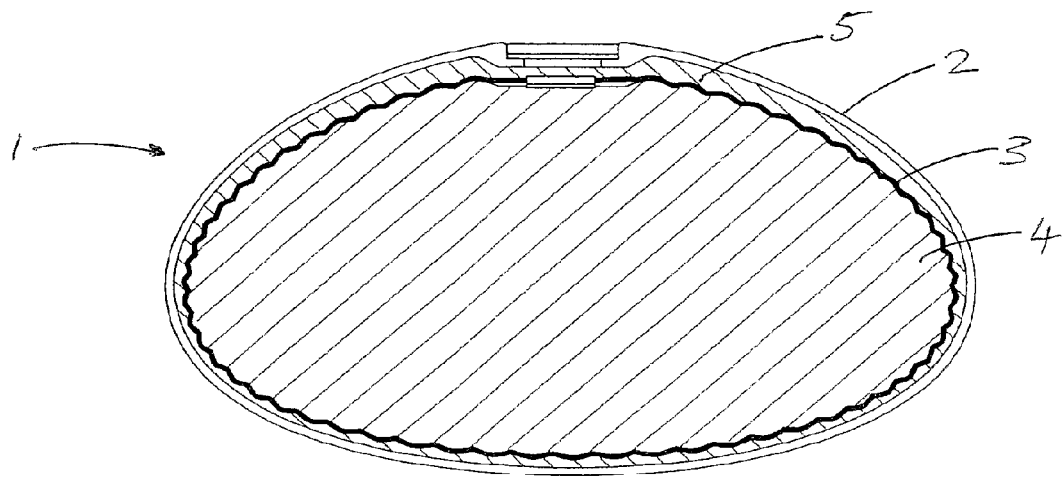
FIG. 1 is a sectional view of an embodiment of a human mammary prosthesis according to the invention.

A preferred embodiment of a human mammary prosthesis (1) according to the invention is shown in FIG. 1. This prosthesis (1) includes a resilient shell (2), which forms an outer container, and within which an inner container (3) is located. The inner container (3) contains the filler material, in this embodiment a saline solution (4), of the prosthesis (1). A lubricant (5) is located between the inner container (3) and shell (2).

Figure 2:
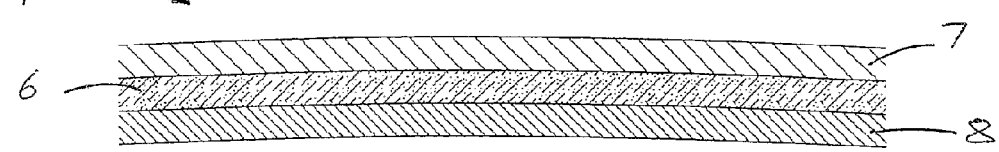
FIG. 2 is a sectional view of a first embodiment of a laminate used for the inner container of the prosthesis of FIG. 1.

The inner container (3) of the prosthesis of FIG. 1 comprises a laminate, as shown in FIG. 2, of a nylon layer (6) which is sandwiched between polyester layer (7) and a polyethylene layer (8). This composite inner layer (9) which forms the inner container (3) is non-permeable to at least the saline solution filler material (4) of the prosthesis (1) and body fluids of the recipient of the prosthesis (1).

The inner layer (3) is effective in limiting the passage of the saline solution (3) from the prosthesis (1) to the body of a recipient thereof. It also limits the ingress of body fluids from the recipient into the prosthesis (1). The inner layer (3) therefore acts as an osmotic barrier which reduces the osmotic driving force which seeks to balance the concentrations of solutes on opposite sides of the barrier, in this case the shell (2), of the prosthesis (1).

It is also possible to construct the inner and outer containers of a prosthesis according to a second embodiment. In this second embodiment of a prosthesis according to the invention shown in FIG. 3, the prosthesis (not shown) includes a filler material in the form of a polyvinyl pyrrolidone (PVP) based fluid (not shown). The PVP is a water soluble polymer and is hydrophilic, which means that it easily bonds with water by means of a hydrogen bond. In this way, the PVP is easily dissolved in water to form the filler material for this embodiment.

The inner container (10) is formed by the inner layer (11), which comprises polyethylene. The PVP based fluid does not move through the polyethylene inner layer (11) under force of osmosis and the inner container (10) therefore provides an effective barrier to prevent loss of the fluid from the prosthesis.

Figure 3:
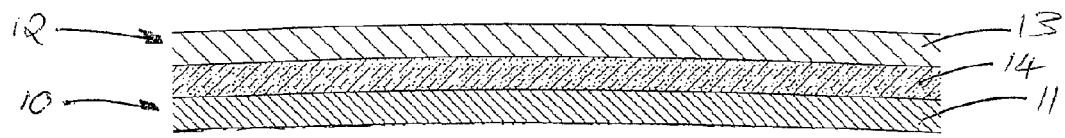
FIG. 3 is a sectional view of a second embodiment of layers used for the inner and outer containers of a human mammary prosthesis of FIG. 1.

FIG. 3 shows the general construction of the layers of the prosthesis, namely the outer layer (13) which forms the shell (12) which contains the entire contents of the prosthesis. Below the outer layer (13) is the inner layer (11) which is separated from the outer layer (13) by a layer of lubricant (14), which is the same as the fluid used as the filler material in the inner container (10).

Figure 4:
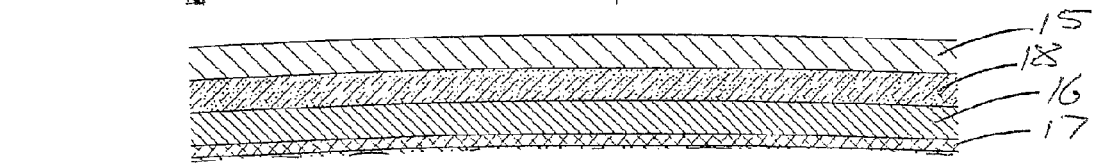
FIG. 4 is a sectional view of a third embodiment of layers used for the inner and outer containers of a human mammary prosthesis of FIG. 1.

FIG. 4 shows a third embodiment of a construction of inner and outer containers for a prosthesis according to the invention, which comprises an outer layer (15). Below this outer layer (15) there is an inner layer (16) comprised of polyethylene which carries a layer of aluminium (17). The aluminium layer (17) is adhered to the polyethylene inner layer (16) by means of a vapour deposition process. Between the inner layer (16) and the outer layer (15) there is a layer of lubricant (18) which is comprised of a mixture of glycerine and water.

The laminate (19) shown in FIG. 4 has a total thickness of about 48 micron, with the vapour deposited aluminium layer having a thickness in the range of about 12 micron to 18 micron. The total thickness of the laminate (19) may vary between about 20 micron and about 70 micron.

In use the prosthesis (1) is implanted in the normal manner into a female patient's breast. The prosthesis (1) is surgically implanted using normal surgical techniques.

It will be appreciated that the embodiments described above are not exhaustive of the invention and it is possible to alter some aspects of the prostheses without departing from the scope of the invention.

It is also possible to include a data transmission device, typically in the form of a transponder or Radio Frequency Identification tag, in the prosthesis. This RFID will be loaded with information relating to the prosthesis, including the size of the prosthesis, date of manufacture, and date of implanting into the patient. It may also be used to store the name of the patient, medical fund details of the patient, and emergency contact details relating to the patient. It is envisaged that this will allow a surgeon to establish the exact nature of the prosthesis without any invasive techniques. In the event of failure of the prosthesis, such as in a motor vehicle accident, where the patient may not be in position to convey critical information about the prosthesis an RFID scanner may be used to obtain information form the patient and perform any necessary procedure. This will also be helpful where a patient wishes to have a set of prostheses changed, for example for a larger set. In most instances, patients do not remember the details such as type, manufacturer, and size of prosthesis. A surgeon then needs to have a range of prostheses on hand during the procedure to replace the prosthesis. If the surgeon knew the type of the original set of prostheses and their sizes, it becomes much easier and quicker to replace them. It is envisaged that the RFID tag will be secured inside the shell. The surgeon will use a commercially available RFID scanner to energize the RFID tag, which triggers it to transmit the data stored on it. This data carrying signal is then received by the scanner and interpreted by custom software operated on the scanner. The information contained in the RFID tag is then displayed on a display screen of the scanner, or printed out.

In the same manner it will be possible to write information to the RFID tag. In this way the data stored on it may be updated, for example with the name of the patient, the date on which the prosthesis was implanted, the medical fund details of the patient and so forth.

It is also possible that the RFID tag may simply transmit a unique identification number and that the relevant details of the patient may be obtained from a secure computer server available on a network, typically the Internet. A physician will then log onto the secure server, enter the unique identification number obtained with the scanner and obtain information about the patient and the prosthesis from the server.

The invention claimed is:

1. A human prosthesis comprising a resilient shell at least partly filled with a fluid based filler material, the shell comprising at least one resilient layer and at least one layer being substantially non-permeable with respect to at least the filler material of the shell and the filler material is fluid based wherein the resilient layer forms a sealed outer container having a surface area and the non-permeable layer forms an inner container having a surface area and wherein the non-permeable layer comprises a composite of a nylon layer located between a polyester and polyethylene.

2. A prosthesis as claimed in claim 1 which comprises a mammary prosthesis.

3. A prosthesis as claimed in claim 1 in which the resilient layer comprises a sealed operatively outer container, the non-permeable layer comprises a sealed operatively inner container which contains the filler material and the inner container is contained by the outer container, which includes a lubricant between the inner container and outer container, and the non-permeable layer is non-permeable also with respect to body fluids.

4. A prosthesis as claimed in claim 1 in which the surface area of the inner container is greater than the surface area of the outer container.

5. A prosthesis as claimed in claim 1 in which the surface area of the inner container is twice as large as the surface area of the outer container.

6. A prosthesis as claimed in claim 1 in which the surface area of the inner container is at least as great as the maximum surface area to which the outer container may be stretched elastically.

7. A prosthesis as claimed in claim 4 in which the water soluble polymer or hydrogel comprises polyvinyl pyrrolidone (PVP) and the non-permeable layer includes at least a polyethylene layer.

8. A prosthesis as claimed in claim 5 in which the hydrophilic polymer is mixed with a saline solution.

9. A prosthesis comprising a resilient shell at least partly filled with a fluid based filler material, the shell comprising at least one resilient layer and at least one layer being substantially non-permeable with respect to at least the filler of the shell and the filler material is fluid based in which the non-permeable layer comprise a composite layer which comprises at least a composite polyethylene and aluminium layer, the filler material includes glycerine, and preferably a combination of water and glycerine.

10. A prosthesis as claimed in claim 9 in which the aluminium layer comprises a vapor deposited layer on the polyethylene layer, and the vapor deposited aluminium layer has a thickness in the range of about 12 microns to 18 microns.

11. A prosthesis as claimed in claim 9 in which the non-permeable layer has a thickness of between about 20 micron and about 70 micron.

12. A prosthesis as claimed in claim 9 in which the non-permeable layer has a thickness of between about 40 micron and 55 micron.

13. A prosthesis as claimed in claim 9 in which the non-permeable layer has a thickness of about 48 micron.

14. A prosthesis as claimed in claim 1 which includes identification means hearing data relating to at least the size of the prosthesis by means of a unique number which is relatable to unique data stored in a database, and for the identification means to include a remotely activatable data transponder configured to transmit a predetermined data carrying signal in response to remote activation thereof by means of an energy field.

15. A prosthesis as claimed in claim 1 in which the shell has a predetermined shape corresponding to that of a breast.

\* \* \* \* \*